United States Patent
Sloo et al.

(10) Patent No.: US 10,416,143 B2
(45) Date of Patent: Sep. 17, 2019

(54) DEVICES AND METHODS FOR DETERMINING AND ACTING UPON CUMULATIVE EXPOSURE OF A BUILDING OCCUPANT TO A HAZARDOUS SUBSTANCE

(71) Applicant: Google LLC, Mountain View, CA (US)

(72) Inventors: David Sloo, Menlo Park, CA (US); Yoky Matsuoka, Los Altos Hills, CA (US)

(73) Assignee: GOOGLE LLC, Mountain View, CA (US)

( * ) Notice: Subject to any disclaimer, the term of this patent is extended or adjusted under 35 U.S.C. 154(b) by 848 days.

(21) Appl. No.: 14/672,001

(22) Filed: Mar. 27, 2015

(65) Prior Publication Data

US 2016/0282320 A1  Sep. 29, 2016

(51) Int. Cl.
*G01N 33/00* (2006.01)
*G08B 21/14* (2006.01)

(52) U.S. Cl.
CPC ......... *G01N 33/0063* (2013.01); *G08B 21/14* (2013.01)

(58) Field of Classification Search
CPC .................................................... G08B 21/14
See application file for complete search history.

(56) References Cited

U.S. PATENT DOCUMENTS

2007/0120693 A1  5/2007  Vij
2013/0181617 A1  7/2013  Maddox
2013/0201316 A1*  8/2013  Binder .................... H04L 67/12
                                                                  348/77
2014/0101082 A1  4/2014  Matsuoka et al.
2015/0077737 A1  3/2015  Belinsky et al.

FOREIGN PATENT DOCUMENTS

JP           05-099778          4/1993

OTHER PUBLICATIONS

Google Inc., Int. Search Report/Written Opinion PCT/US2016/024561, dated Jun. 27, 2016, 11 pgs.

(Continued)

*Primary Examiner* — Yu-Hsi D Sun
(74) *Attorney, Agent, or Firm* — Morgan, Lewis & Bockius LLP

(57) ABSTRACT

A computing system performs a method of determining cumulative exposure to a gas. The computing system receives data that correspond to local concentrations of a gas from a plurality of stationary gas sensors in a home. Respective stationary gas sensors are located at respective fixed locations in respective rooms in the home. The computing system also receives data that correspond to occupancy of the home, including occupancy by a first occupant. The computing system determines a cumulative exposure of the first occupant to the gas in the home, based at least in part on the received data that correspond to local concentrations of the gas and the received data that correspond to occupancy of the home. The computing system performs and/or sends instructions to perform one or more predefined operations in accordance with the determined cumulative exposure of the first occupant.

16 Claims, 12 Drawing Sheets

(56) References Cited

OTHER PUBLICATIONS

Criteria for a Recommended Standard . . . , Occupational Exposure to Carbon Monoxide, U.S. Department of Health, Education and Welfare, 1972, 24 pgs.
Fadell, U.S. Appl. No. 61/887,963, filed Oct. 7, 2013, 227 pgs.
Lung Cancer Risks from Radon, RadonSeal, www.radonseal.com/radon-health-risks.htm, 2014, printed from Internet Oct. 1, 2014, 4 pgs.
Overton, Dosimetry Modeling of Inhaled Toxic Reactive Gases, Air Pollution, the Automobile, and Public Health, National Academies Press, Washington DC, 1988, 20 pgs.
Sales, Multi-Sensor Person Following in Low-Visibility Scenarios, Sensors 2010, vol. 10, Dec. 3, 2010, pp. 10953-10966.
US EPA, Acute Exposure Guideline Levels (AEGLs), Carbon Monoxide Levels, www.epa.gov/oppt/aegl/pubs/results50.htm, Jan. 11, 2012, 1 pg.
Xiang, A Hybrid Sensor System for Indoor Air Quality Monitoring, 2013 IEEE International Conference on Distributed Computing in Sensor Systems (DCOSS), Cambridge, MA, May 20-23, 2013, 9 pgs.
Xiang, Mobile Sensor Network Design and Optimization for Air Quality Monitoring, Univ. of Michigan, 2014, 132 pgs.

\* cited by examiner

DEVICES AND METHODS FOR DETERMINING AND ACTING UPON CUMULATIVE EXPOSURE OF A BUILDING OCCUPANT TO A HAZARDOUS SUBSTANCE

TECHNICAL FIELD

This relates generally to detecting hazardous substances, including but not limited to determining cumulative exposure of a building occupant to a hazardous substance.

BACKGROUND

Hazardous substances (e.g., toxic/noxious gasses and/or harmful particulates) may be present in the air in a building (e.g., a house). Exposure of a building occupant to hazardous substances may be harmful to the occupant's health. Detectors may be used to determine instantaneous levels of various hazardous substances. Mere knowledge of instantaneous levels of hazardous substances, however, does not quantify the cumulative exposure of the occupant to the hazardous substances, and therefore may not provide a useful indication of the health risk to the occupant.

SUMMARY

Accordingly, there is a need for building monitoring systems that can determine cumulative exposure of an occupant to hazardous substances.

In accordance with some embodiments, a method is performed at a computing system. The method includes receiving data that correspond to local concentrations of a gas from a plurality of stationary gas sensors in a home. The stationary gas sensors are located in a plurality of rooms in the home. A respective stationary gas sensor is located at a respective fixed location in a respective room in the home. The method also includes receiving data that correspond to occupancy of the home, including occupancy by a first occupant, and determining a cumulative exposure of the first occupant to the gas in the home. The cumulative exposure is determined based at least in part on the received data that correspond to local concentrations of the gas and the received data that correspond to occupancy of the home. The method further includes performing and/or sending instructions to perform one or more predefined operations in accordance with the determined cumulative exposure of the first occupant.

In accordance with some embodiments, a computing system includes one or more processors, memory, and one or more programs; the one or more programs are stored in the memory and configured to be executed by the one or more processors. The one or more programs include instructions for performing the operations of the method described above. In accordance with some embodiments, a non-transitory computer-readable storage medium has stored therein instructions which when executed by a computing system with one or more processors, cause the computing system to perform the operations of the method described above. In accordance with some embodiments, a computing system includes means for performing the operations of the method described above.

Thus, methods and systems are provided for determining cumulative exposure of a building occupant to hazardous substances. Such methods and systems may complement or replace conventional methods and systems for detecting environmental hazards.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

DESCRIPTION OF EMBODIMENTS

A home or other structure includes stationary sensors that collect data regarding concentrations of a hazardous substance (e.g., toxic gasses or harmful particulates) in various areas (e.g., rooms). This data is used to determine a cumulative exposure of an occupant to the hazardous substance. The occupant or another person (e.g., a caregiver) may be notified of the cumulative exposure or alerted to potentially harmful exposure, and appropriate action may be taken to help the occupant.

Figure 5:
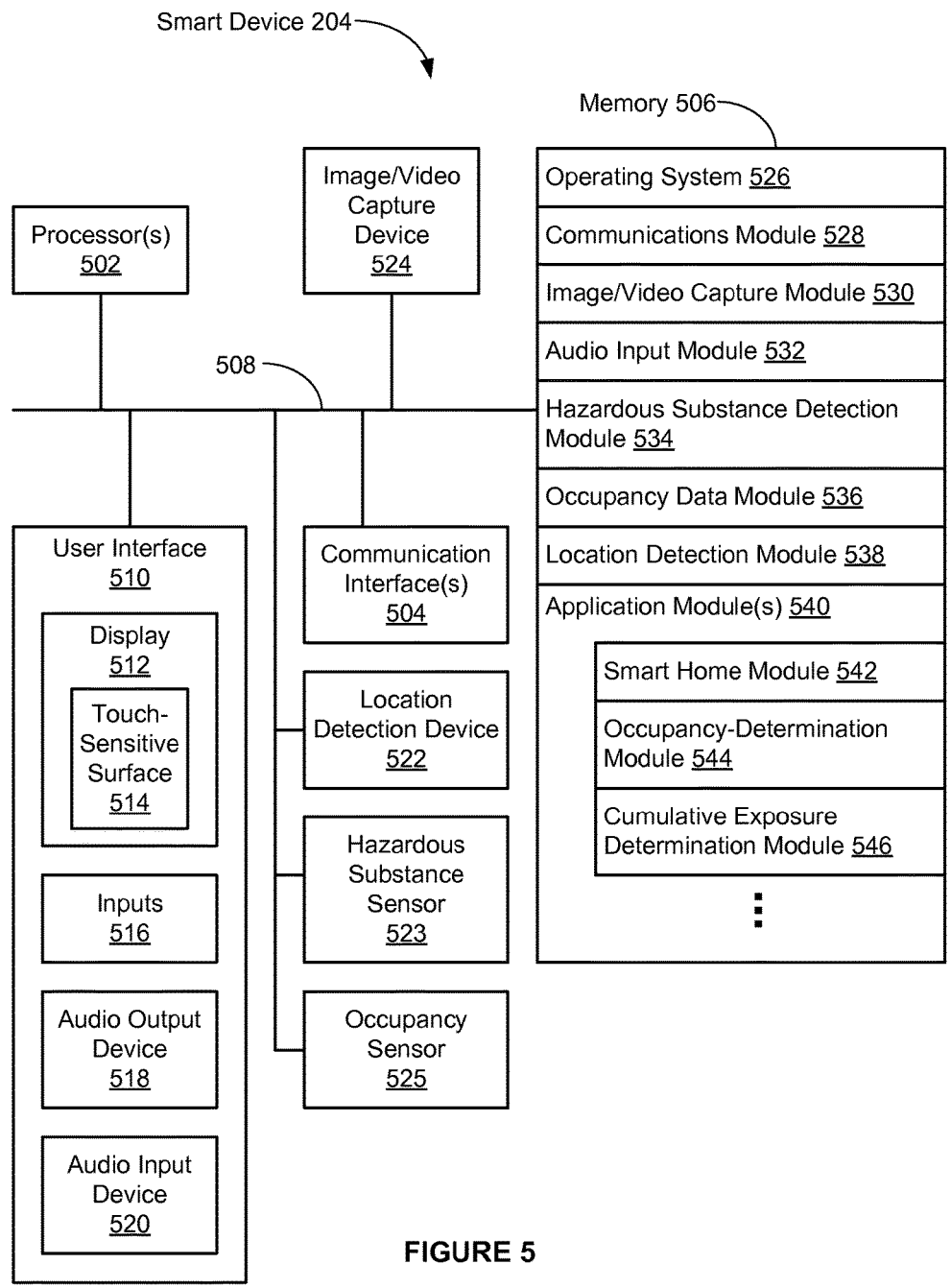
FIG. 5 is a block diagram illustrating an exemplary smart device, such as a smart hazard detector or occupancy sensor, in accordance with some embodiments.
Figure 6:
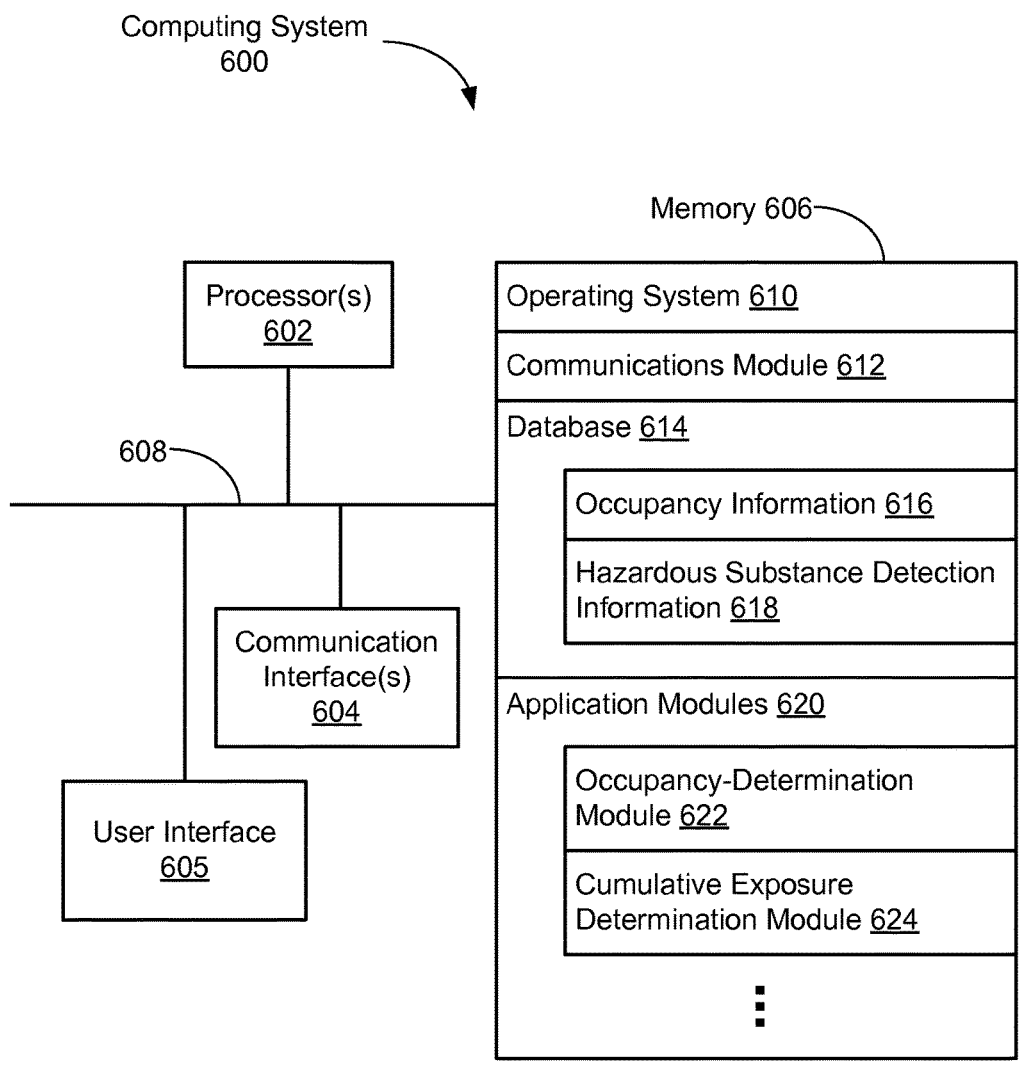
FIG. 6 is a block diagram illustrating an exemplary computing system in accordance with some embodiments.
Figure 7A:
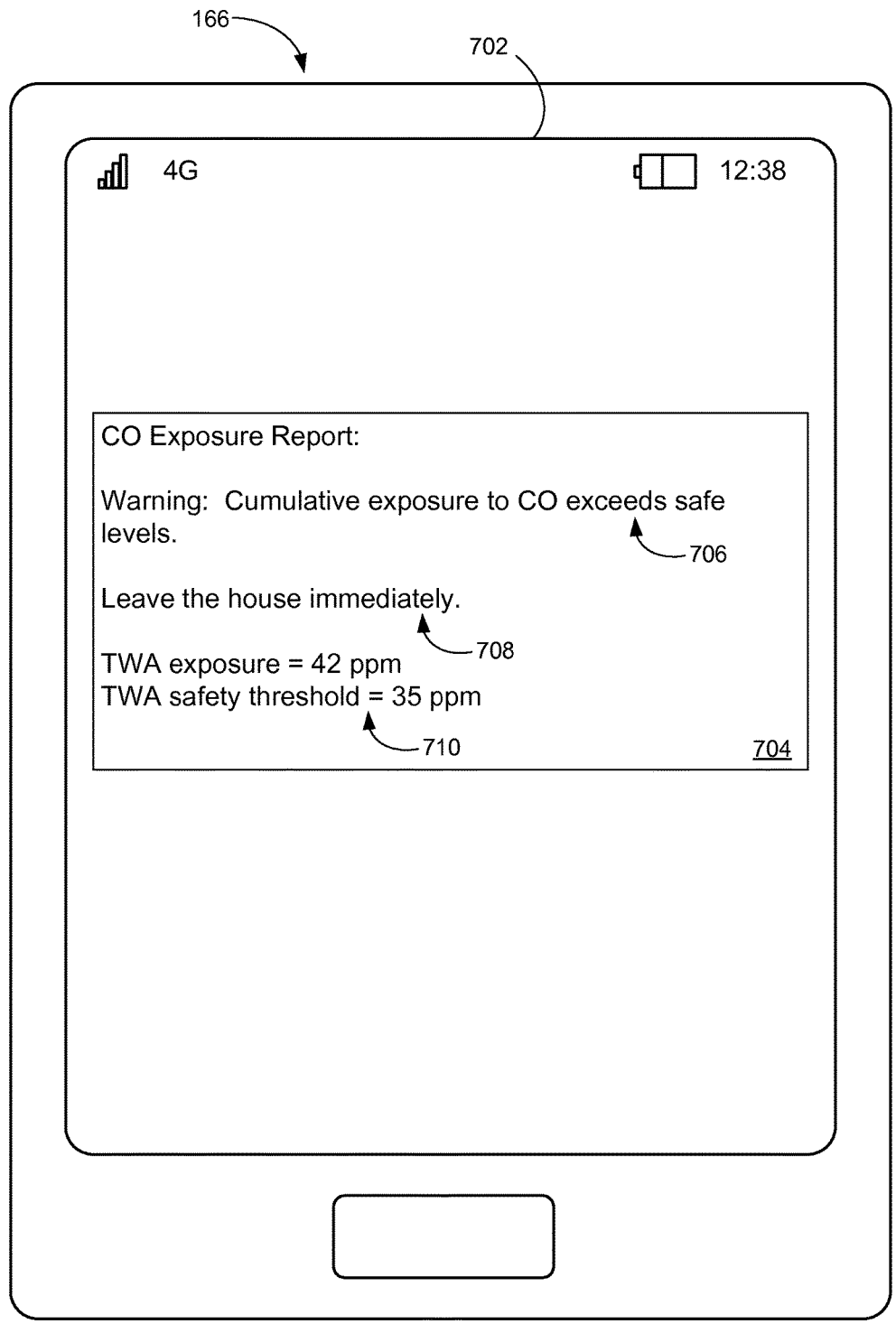
FIGS. 7A-7C illustrate exemplary graphical user interfaces shown on an electronic device in accordance with some embodiments.
Figure 7B:
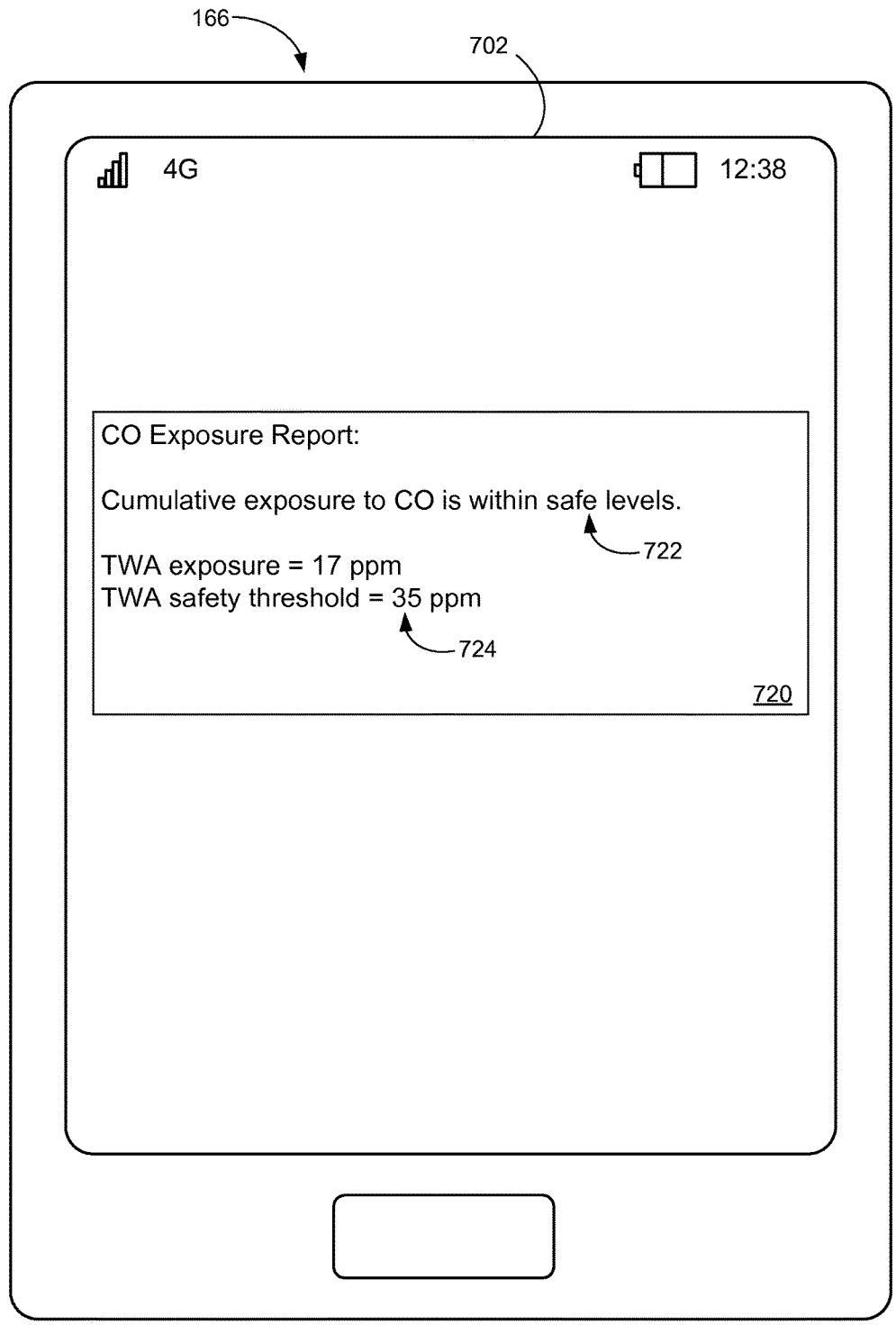
Figure 7C:
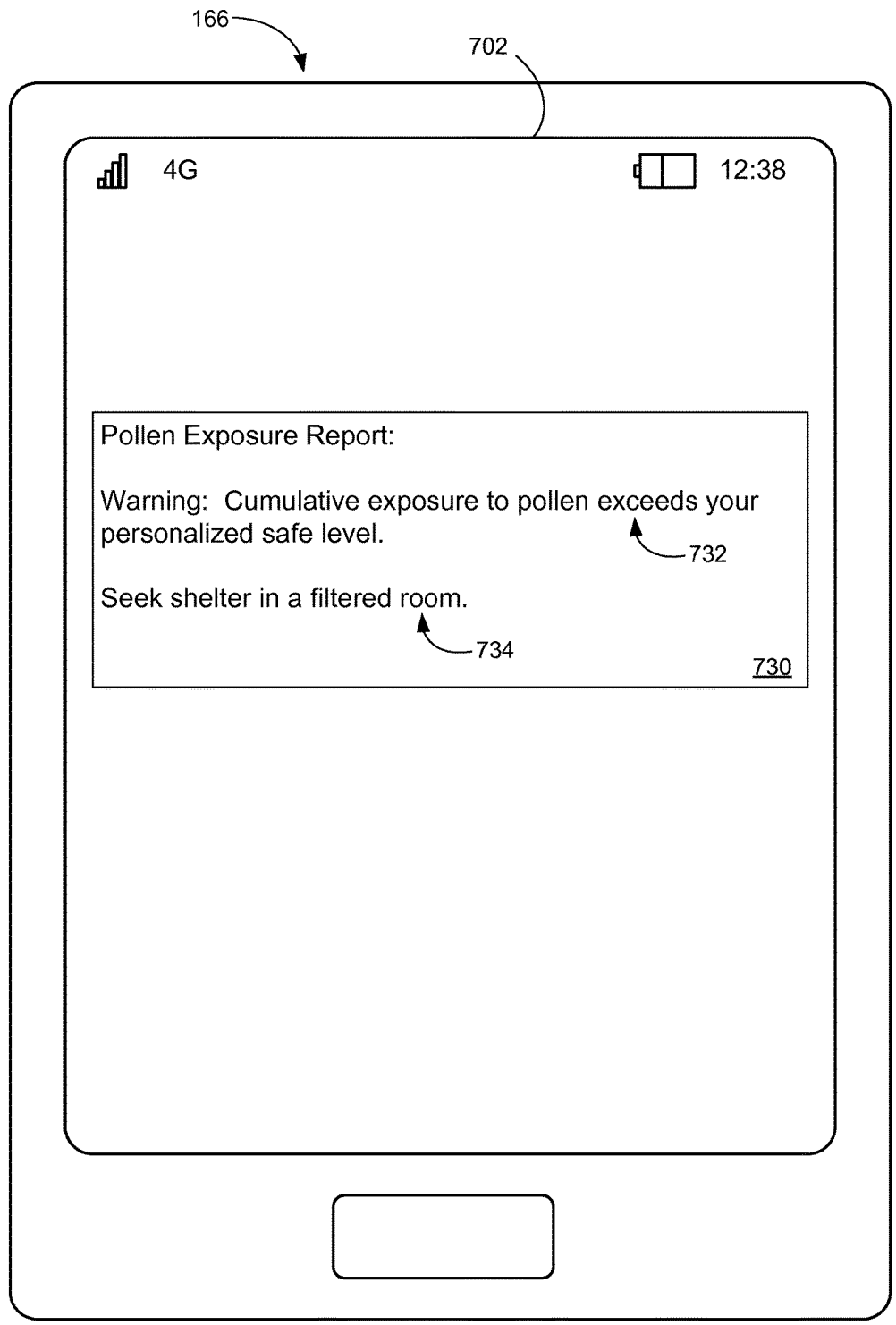
Figure 8:
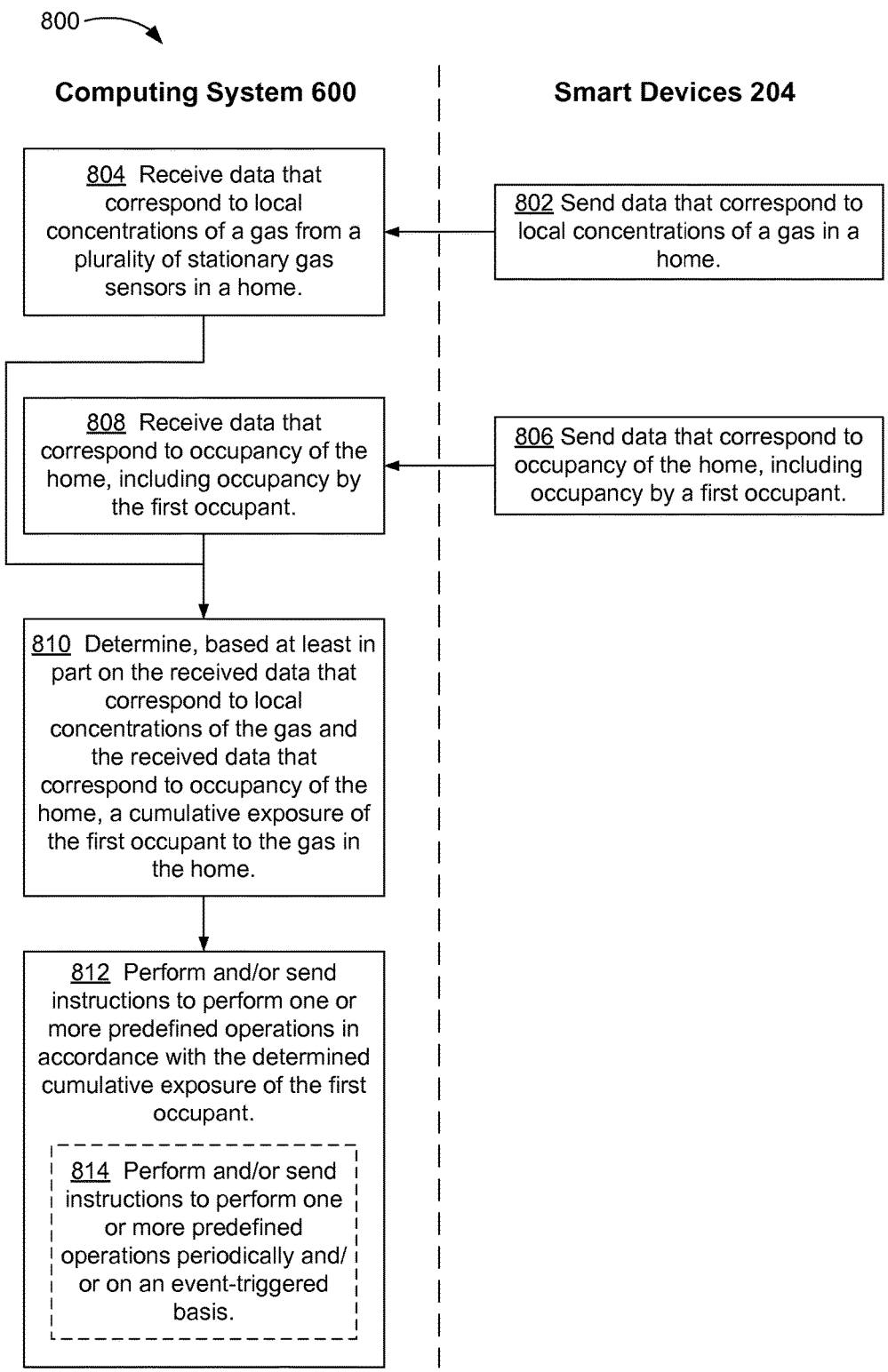
FIGS. 8 and 9A-9B are flow diagrams illustrating methods of determining and acting upon cumulative exposure of a building occupant to a hazardous substance, in accordance with some embodiments.
Figure 9A:
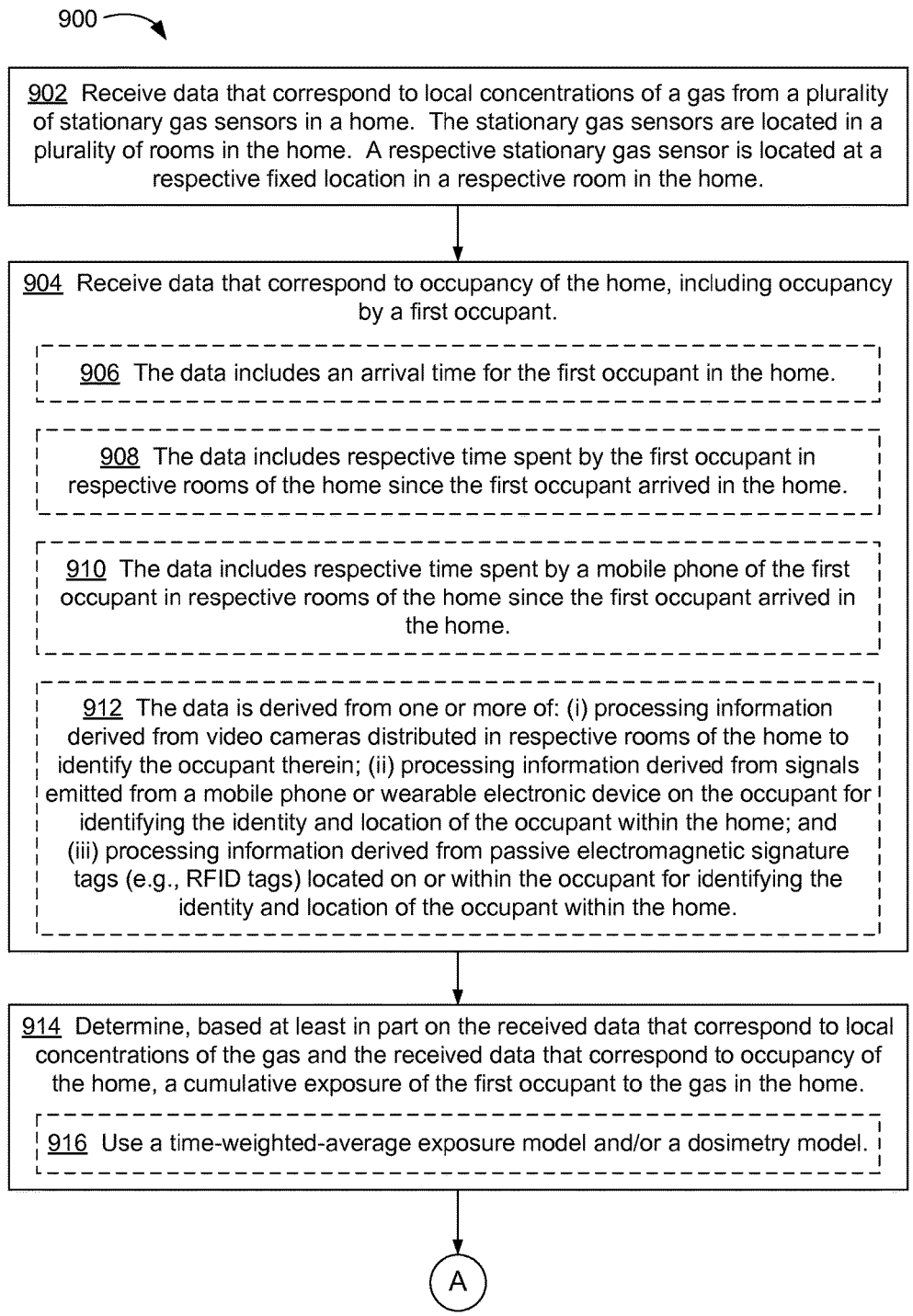
Figure 9B:
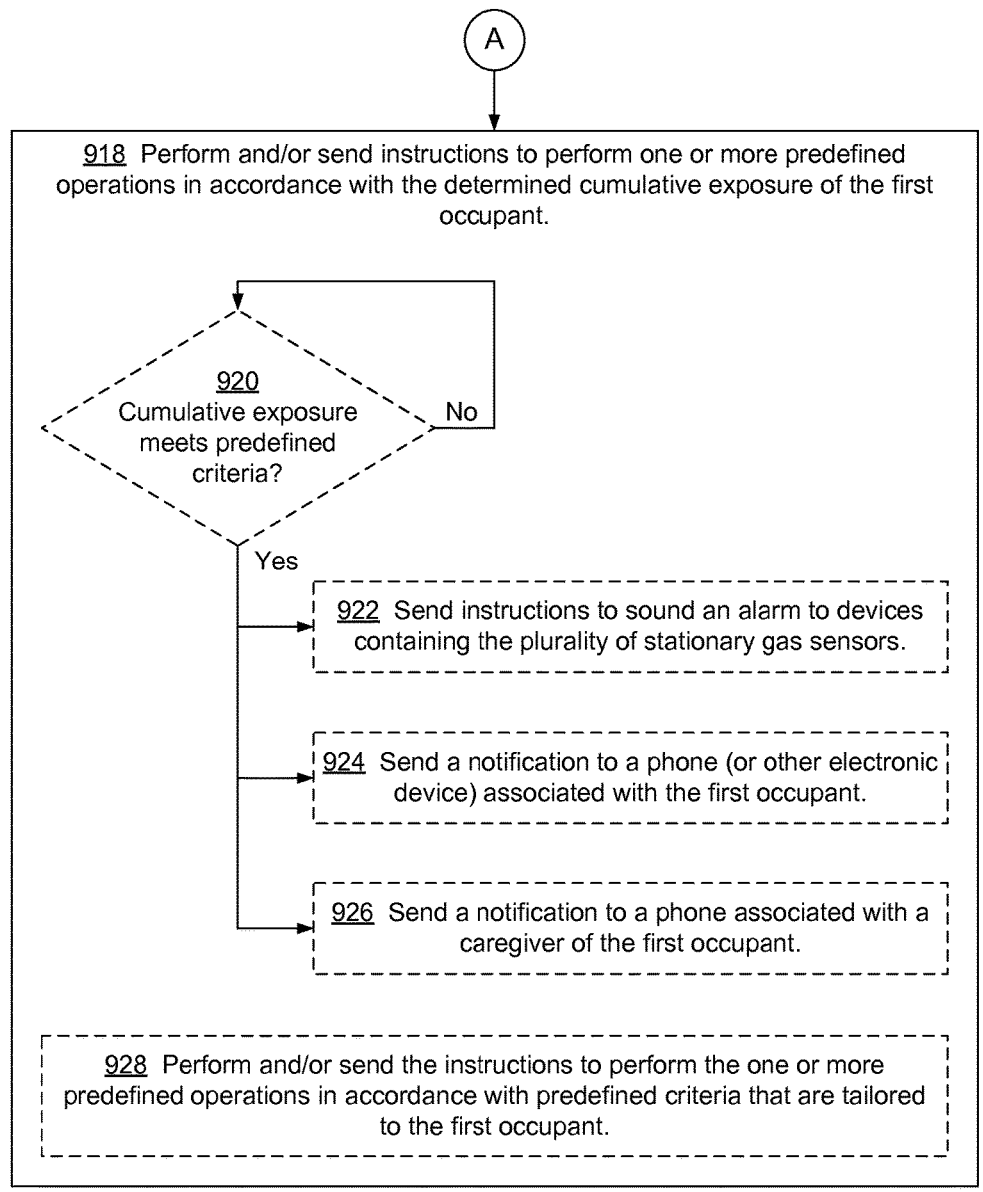

Below, FIGS. 1-4 provide an overview of exemplary smart home device networks and capabilities. FIGS. 5 and 6 are block diagrams of electronic devices included in or in communication with a smart home environment. FIGS. 7A-7C illustrate exemplary user interfaces for displaying information relating to cumulative exposure to hazardous substances that may be present in the smart home environment. FIGS. 8, 9A, and 9B are flow diagrams illustrating methods of taking action based on cumulative exposure to a hazardous substance, in accordance with some embodiments.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

It will also be understood that, although the terms first, second, etc. are, in some instances, used herein to describe various elements, these elements should not be limited by these terms. These terms are only used to distinguish one element from another. For example, a first occupant of a room or structure could be termed a second occupant, and, similarly, a second occupant could be termed a first occupant, without departing from the scope of the various described embodiments. The first occupant and the second occupant are both occupants, but they are not the same occupant.

The terminology used in the description of the various described embodiments herein is for the purpose of describing particular embodiments only and is not intended to be limiting. As used in the description of the various described embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

It is to be appreciated that "smart home environments" may refer to smart environments for homes such as a single-family house, but the scope of the present teachings is not so limited. The present teachings are also applicable, without limitation, to duplexes, townhomes, multi-unit apartment buildings, hotels, retail stores, office buildings, industrial buildings, and more generally any living space or work space.

It is also to be appreciated that while the terms user, customer, installer, homeowner, occupant, guest, tenant, landlord, repair person, and the like may be used to refer to the person or persons acting in the context of some particularly situations described herein, these references do not limit the scope of the present teachings with respect to the person or persons who are performing such actions. Thus, for example, the terms user, customer, purchaser, installer, subscriber, and homeowner may often refer to the same person in the case of a single-family residential dwelling, because the head of the household is often the person who makes the purchasing decision, buys the unit, and installs and configures the unit, and is also one of the users of the unit. However, in other scenarios, such as a landlord-tenant environment, the customer may be the landlord with respect to purchasing the unit, the installer may be a local apartment supervisor, a first user may be the tenant, and a second user may again be the landlord with respect to remote control functionality. Importantly, while the identity of the person performing the action may be germane to a particular advantage provided by one or more of the embodiments, such identity should not be construed in the descriptions that follow as necessarily limiting the scope of the present teachings to those particular individuals having those particular identities.

Figure 1:
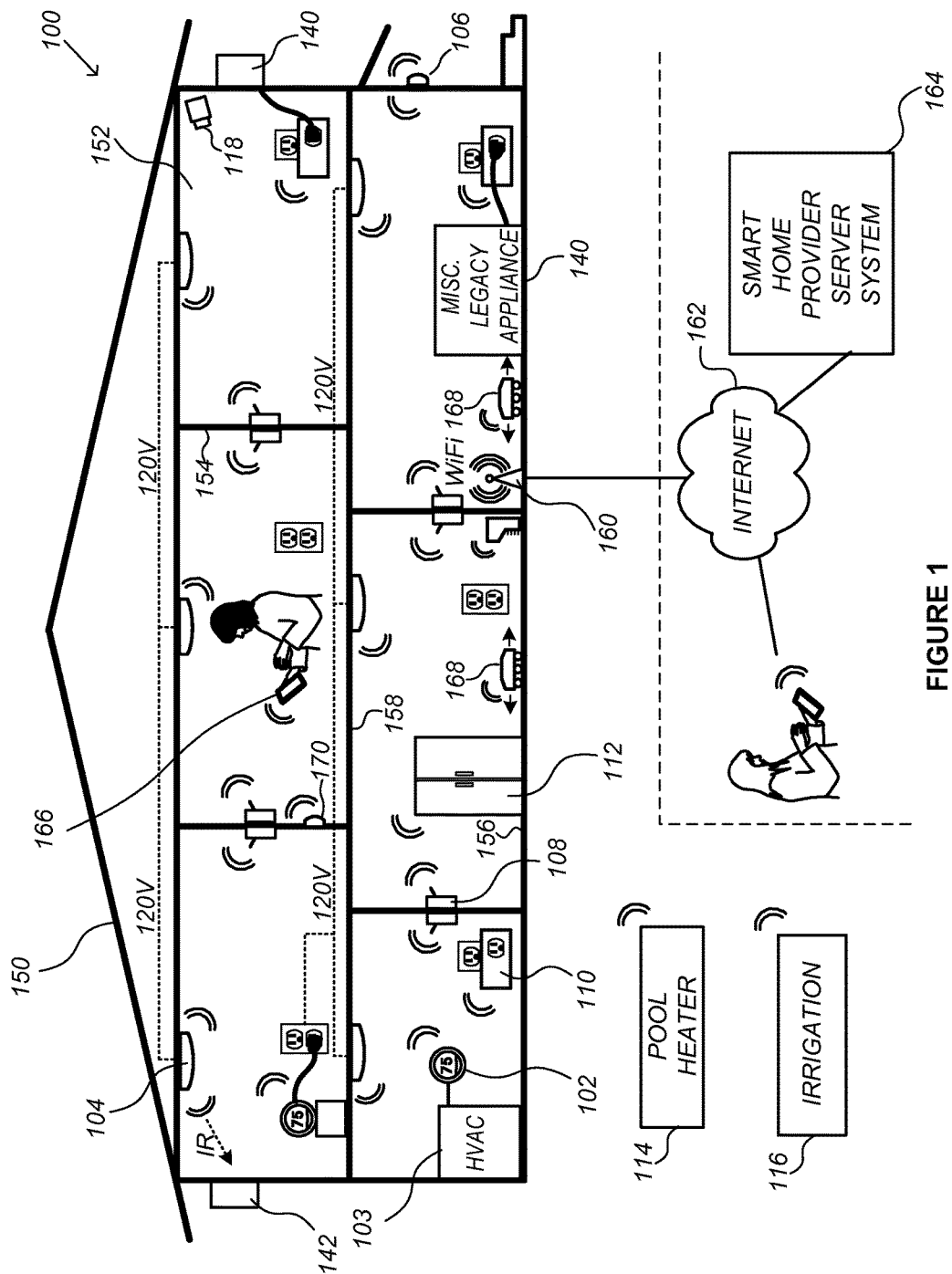
FIG. 1 is an exemplary smart home environment in accordance with some embodiments.

FIG. 1 is an exemplary smart home environment 100 in accordance with some embodiments. Smart home environment 100 includes a structure 150 (e.g., a house, office building, garage, or mobile home) with various integrated devices. It will be appreciated that devices may also be integrated into a smart home environment 100 that does not include an entire structure 150, such as an apartment, condominium, or office space. Further, the smart home environment 100 may control and/or be coupled to devices outside of the actual structure 150. Indeed, several devices in the smart home environment 100 need not be physically within the structure 150. For example, a device controlling a pool heater 114 or irrigation system 116 may be located outside of structure 150.

The depicted structure 150 includes a plurality of rooms 152, separated at least partly from each other via walls 154. The walls 154 may include interior walls or exterior walls. Each room may further include a floor 156 and a ceiling 158. Devices may be mounted on, integrated with and/or supported by a wall 154, floor 156 or ceiling 158.

In some embodiments, the integrated devices of the smart home environment 100 include intelligent, multi-sensing, network-connected devices that integrate seamlessly with each other in a smart home network (e.g., 202 FIG. 2) and/or with a central server or a cloud-computing system to provide a variety of useful smart home functions. The smart home environment 100 may include one or more intelligent, multi-sensing, network-connected thermostats 102 (hereinafter referred to as "smart thermostats 102"), one or more intelligent, network-connected, hazard detection units 104 (hereinafter referred to as "smart hazard detectors 104"), and one or more intelligent, multi-sensing, network-connected entryway interface devices 106 (hereinafter referred to as "smart doorbells 106"). In some embodiments, the smart thermostat 102 detects ambient climate characteristics (e.g., temperature and/or humidity) and controls a HVAC system 103 accordingly.

The smart hazard detectors 104 may detect the presence of a hazardous substance (e.g., pollutant) or a substance indicative of a hazardous substance. In some embodiments, the smart hazard detectors 104 include gas sensors that detect one or more toxic/noxious gasses (e.g., carbon monoxide, radon, volatile organic compounds, etc.). In some embodiments, the smart hazard detectors 104 include particulate detectors that detect one or more types of harmful particulates (e.g., smoke, mold, pollen, etc.). Smart hazard detectors 104 may be located in some or all of the rooms 152 of the structure 150.

The smart doorbell 106 may detect a person's approach to or departure from a location (e.g., an outer door), control doorbell functionality, announce a person's approach or departure via audio or visual means, and/or control settings on a security system (e.g., to activate or deactivate the security system when occupants go and come).

In some embodiments, the smart home environment 100 includes one or more intelligent, multi-sensing, network-connected wall switches 108 (hereinafter referred to as "smart wall switches 108"), along with one or more intelligent, multi-sensing, network-connected wall plug interfaces 110 (hereinafter referred to as "smart wall plugs 110"). The smart wall switches 108 may detect ambient lighting conditions, detect room-occupancy states, and control a power and/or dim state of one or more lights. In some instances, smart wall switches 108 may also control a power state or speed of a fan, such as a ceiling fan. The smart wall plugs 110 may detect occupancy of a room or enclosure and control supply of power to one or more wall plugs (e.g., such that power is not supplied to the plug if nobody is at home).

In some embodiments, the smart home environment 100 of FIG. 1 includes a plurality of intelligent, multi-sensing, network-connected appliances 112 (hereinafter referred to as "smart appliances 112"), such as refrigerators, stoves, ovens, televisions, washers, dryers, lights, stereos, intercom systems, garage-door openers, floor fans, ceiling fans, wall air conditioners, pool heaters, irrigation systems, security systems, space heaters, window AC units, motorized duct vents, and so forth. In some embodiments, when plugged in, an appliance may announce itself to the smart home network, such as by indicating what type of appliance it is, and it may automatically integrate with the controls of the smart home. Such communication by the appliance to the smart home may be facilitated by either a wired or wireless communication protocol. The smart home may also include a variety of non-communicating legacy appliances 140, such as old conventional washer/dryers, refrigerators, and the like, which may be controlled by smart wall plugs 110. The smart home environment 100 may further include a variety of partially communicating legacy appliances 142, such as infrared ("IR") controlled wall air conditioners or other IR-controlled devices, which may be controlled by IR signals provided by the smart hazard detectors 104 or the smart wall switches 108.

In some embodiments, the smart home environment 100 includes one or more network-connected cameras 118 that are configured to provide video monitoring and security in the smart home environment 100. The cameras 118 may be used to determine occupancy of the structure 150 and/or particular rooms 152 in the structure 150, and thus may act as occupancy sensors. For example, video captured by the cameras 118 may be processed to identify the presence of an occupant in the structure 150 (e.g., in a particular room 152). Specific individuals may be identified based, for example, on their appearance (e.g., height, face) and/or movement (e.g., their walk/gate). The smart home environment 100 may additionally or alternatively include one or more other occupancy sensors (e.g., the smart doorbell 106, smart doorlocks, touch screens, IR sensors, microphones, ambient light sensors, motion detectors, smart nightlights 170, etc.). In some embodiments, the smart home environment 100 includes radio-frequency identification (RFID) readers (e.g., in each room 152 or a portion thereof) that determine occupancy based on RFID tags located on or embedded in occupants. For example, RFID readers may be integrated into the smart hazard detectors 104.

The smart home environment 100 may also include communication with devices outside of the physical home but within a proximate geographical range of the home. For example, the smart home environment 100 may include a pool heater monitor 114 that communicates a current pool temperature to other devices within the smart home environment 100 and/or receives commands for controlling the pool temperature. Similarly, the smart home environment 100 may include an irrigation monitor 116 that communicates information regarding irrigation systems within the smart home environment 100 and/or receives control information for controlling such irrigation systems.

By virtue of network connectivity, one or more of the smart home devices of FIG. 1 may further allow a user to interact with the device even if the user is not proximate to the device. For example, a user may communicate with a device using a computer (e.g., a desktop computer, laptop computer, or tablet) or other portable electronic device (e.g., a mobile phone, such as a smart phone) 166. A webpage or application may be configured to receive communications from the user and control the device based on the communications and/or to present information about the device's operation to the user. For example, the user may view a cumulative exposure to a hazard (e.g., a toxic/noxious gas or harmful airborne particulates) as determined using smart hazard detectors 104. In another example, the user may view and/or adjust a hazard-detection threshold for a smart hazard detector 104. The user may be inside or outside the structure 150 during this remote communication.

As discussed above, users may control smart devices in the smart home environment 100 using a network-connected computer or portable electronic device 166. In some examples, some or all of the occupants (e.g., individuals who live in the home) may register their device 166 with the smart home environment 100. Such registration may be made at a central server to authenticate the occupant and/or the device as being associated with the home and to give permission to the occupant to use the device to control the smart devices in the home. An occupant may use their registered device 166 to remotely control the smart devices of the home, such as when the occupant is at work or on vacation. The occupant may also use their registered device to control the smart devices when the occupant is actually located inside the home, such as when the occupant is sitting on a couch inside the home. It should be appreciated that instead of or in addition to registering devices 166, the smart home environment 100 may make inferences about which individuals live in the home and are therefore occupants and which devices 166 are associated with those individuals. As such, the smart home environment may "learn" who is an occupant and permit the devices 166 associated with those individuals to control the smart devices of the home.

In some embodiments, in addition to containing processing and sensing capabilities, devices 102, 104, 106, 108, 110, 112, 114, 116 and/or 118 (collectively referred to as "the smart devices") are capable of data communications and information sharing with other smart devices, a central server or cloud-computing system, and/or other devices that are network-connected. Data communications may be carried out using any of a variety of custom or standard wireless protocols (e.g., IEEE 802.15.4, Wi-Fi, ZigBee, 6LoWPAN, Thread, Z-Wave, Bluetooth Smart, ISA 100.11a, WirelessHART, MiWi, etc.) and/or any of a variety of custom or standard wired protocols (e.g., Ethernet, HomePlug, etc.), or any other suitable communication protocol, including communication protocols not yet developed as of the filing date of this document.

In some embodiments, the smart devices serve as wireless or wired repeaters. In some embodiments, a first one of the smart devices communicates with a second one of the smart devices via a wireless router. The smart devices may further communicate with each other via a connection (e.g., network interface 160) to a network, such as the Internet 162. Through the Internet 162, the smart devices may communicate with a smart home provider server system 164 (also called a central server system and/or a cloud-computing system herein). The smart home provider server system 164 may be associated with a manufacturer, support entity, or service provider associated with the smart device(s). In some embodiments, a user is able to contact customer support using a smart device itself rather than needing to use other communication means, such as a telephone or Internet-connected computer. In some embodiments, software updates are automatically sent from the smart home provider server system 164 to smart devices (e.g., when available, when purchased, or at routine intervals).

Figure 2:
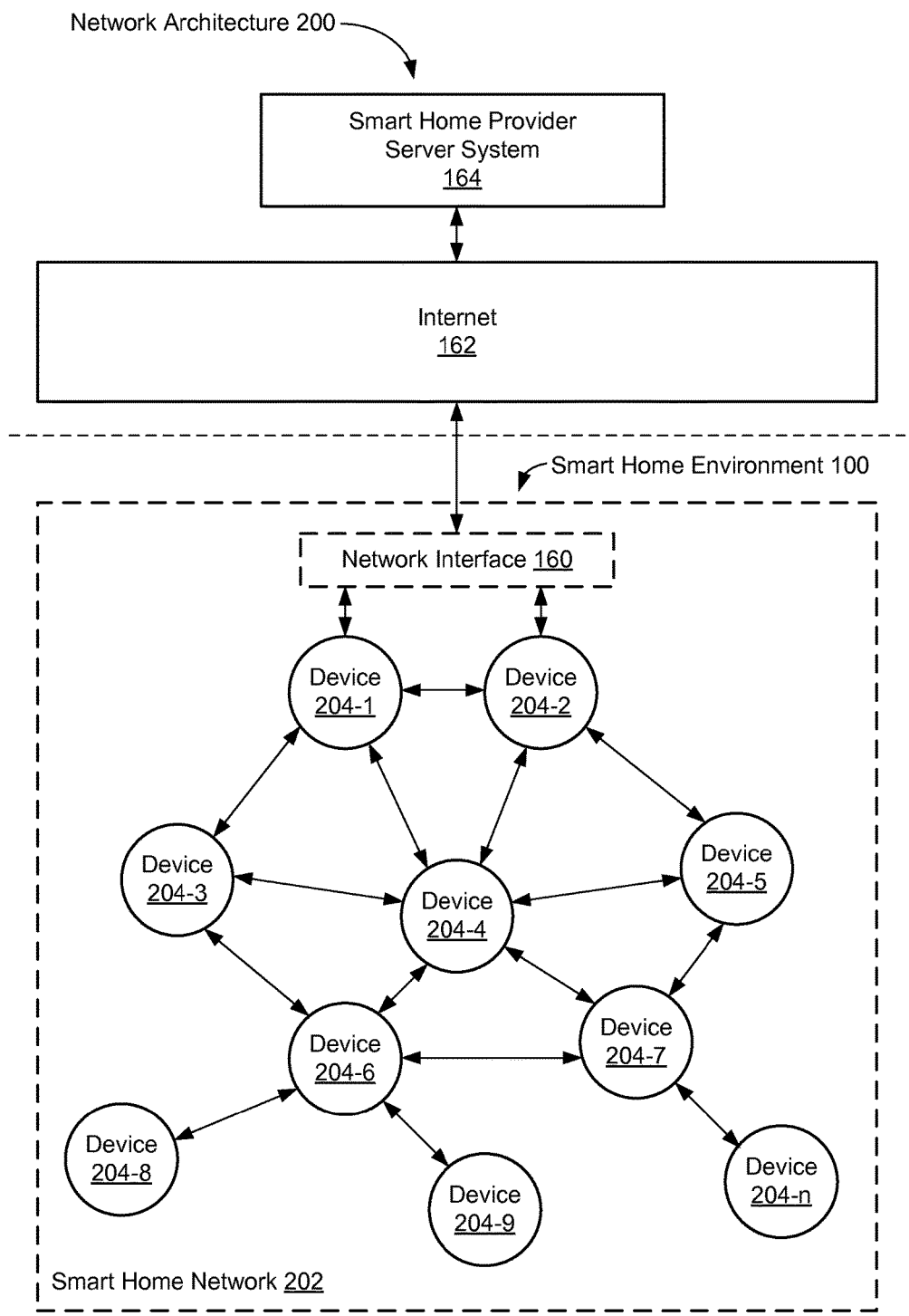
FIG. 2 is a block diagram illustrating an exemplary network architecture that includes a smart home network in accordance with some embodiments.

FIG. 2 is a block diagram illustrating an exemplary network architecture 200 that includes a smart home network 202 in accordance with some embodiments. In some embodiments, the smart devices 204 in the smart home environment 100 (e.g., devices 102, 104, 106, 108, 110, 112, 114, 116 and/or 118) combine to create a mesh network in smart home network 202. In some embodiments, one or more smart devices 204 in the smart home network 202 operate as a smart home controller. In some embodiments, a smart home controller has more computing power than other smart devices. In some embodiments, a smart home controller processes inputs (e.g., from smart devices 204, electronic device 166, and/or smart home provider server system 164) and sends commands (e.g., to smart devices 204 in the smart home network 202) to control operation of the smart home environment 100. In some embodiments, some of the smart devices 204 in the smart home network 202 (e.g., in the mesh network) are "spokesman" nodes (e.g., 204-1) and others are "low-powered" nodes (e.g., 204-9). Some of the smart devices in the smart home environment 100 are battery powered, while others have a regular and reliable power source, such as by connecting to wiring (e.g., to 120V line voltage wires) behind the walls 154 of the smart home environment. The smart devices that have a regular and reliable power source are referred to as "spokesman" nodes. These nodes are typically equipped with the capability of using a wireless protocol to facilitate bidirectional communication with a variety of other devices in the smart home environment 100, as well as with the smart home provider server system 164. In some embodiments, one or more "spokesman" nodes operate as a smart home controller. On the other hand, the devices that are battery powered are the "low-power" nodes. These nodes tend to be smaller than spokesman nodes and typically only communicate using wireless protocols that require very little power, such as Zigbee, 6LoWPAN, etc.

In some embodiments, some low-power nodes are incapable of bidirectional communication. These low-power nodes send messages, but they are unable to "listen". Thus, other devices in the smart home environment 100, such as the spokesman nodes, cannot send information to these low-power nodes.

In some embodiments, some low-power nodes are capable of only a limited bidirectional communication. For example, other devices are able to communicate with the low-power nodes only during a certain time period.

As described, in some embodiments, the smart devices serve as low-power and spokesman nodes to create a mesh network in the smart home environment 100. In some embodiments, individual low-power nodes in the smart home environment regularly send out messages regarding what they are sensing, and the other low-powered nodes in the smart home environment—in addition to sending out their own messages—forward the messages, thereby causing the messages to travel from node to node (i.e., device to device) throughout the smart home network 202. In some embodiments, the spokesman nodes in the smart home network 202, which are able to communicate using a relatively high-power communication protocol, such as IEEE 802.11, are able to switch to a relatively low-power communication protocol, such as IEEE 802.15.4, to receive these messages, translate the messages to other communication protocols, and send the translated messages to other spokesman nodes and/or the smart home provider server system 164 (using, e.g., the relatively high-power communication protocol). Thus, the low-powered nodes using low-power communication protocols are able to send and/or receive messages across the entire smart home network 202, as well as over the Internet 162 to the smart home provider server system 164. In some embodiments, the mesh network enables the smart home provider server system 164 to regularly receive data from most or all of the smart devices in the home, make inferences based on the data, facilitate state synchronization across devices within and outside of the smart home network 202, and send commands back to one or more of the smart devices to perform tasks in the smart home environment.

As described, the spokesman nodes and some of the low-powered nodes are capable of "listening." Accordingly, users, other devices, and/or the smart home provider server system 164 may communicate control commands to the low-powered nodes. For example, a user may use the electronic device 166 (e.g., a smart phone) to send commands over the Internet to the smart home provider server system 164, which then relays the commands to one or more spokesman nodes in the smart home network 202. The spokesman nodes may use a low-power protocol to communicate the commands to the low-power nodes throughout the smart home network 202, as well as to other spokesman nodes that did not receive the commands directly from the smart home provider server system 164.

In some embodiments, a smart nightlight 170 (FIG. 1), which is an example of a smart device 204, is a low-power node. In addition to housing a light source, the smart nightlight 170 houses an occupancy sensor, such as an ultrasonic or passive IR sensor, and an ambient light sensor, such as a photo-resistor or a single-pixel sensor that measures light in the room. In some embodiments, the smart nightlight 170 is configured to activate the light source when its ambient light sensor detects that the room is dark and when its occupancy sensor detects that someone is in the room. In other embodiments, the smart nightlight 170 is simply configured to activate the light source when its ambient light sensor detects that the room is dark. Further, in some embodiments, the smart nightlight 170 includes a low-power wireless communication chip (e.g., a ZigBee chip) that regularly sends out messages regarding the occupancy of the room and the amount of light in the room, including instantaneous messages coincident with the occupancy sensor detecting the presence of a person in the room. As mentioned above, these messages may be sent wirelessly (e.g., using the mesh network) from node to node (i.e., smart device to smart device) within the smart home network 202 as well as over the Internet 162 to the smart home provider server system 164.

Other examples of low-power nodes include battery-operated versions of the smart hazard detectors 104. Low-power smart hazard detectors 104 may be located in an area without access to constant and reliable power and may include any number and type of sensors (e.g., within a single housing), such as smoke/fire/heat sensors, carbon monoxide/dioxide sensors, occupancy/motion sensors, ambient light sensors, temperature sensors, humidity sensors, and the like. Furthermore, smart hazard detectors 104 may send messages that correspond to each of the respective sensors to the other devices and/or the smart home provider server system 164, such as by using the mesh network as described above.

Examples of spokesman nodes include smart doorbells 106, smart thermostats 102, smart wall switches 108, and smart wall plugs 110. These devices 102, 106, 108, and 110 are often located near and connected to a reliable power source, and therefore may include more power-consuming components, such as one or more communication chips capable of bidirectional communication in a variety of protocols.

In some embodiments, the smart home environment 100 includes service robots 168 (FIG. 1) that are configured to carry out, in an autonomous manner, any of a variety of household tasks.

Figure 3:
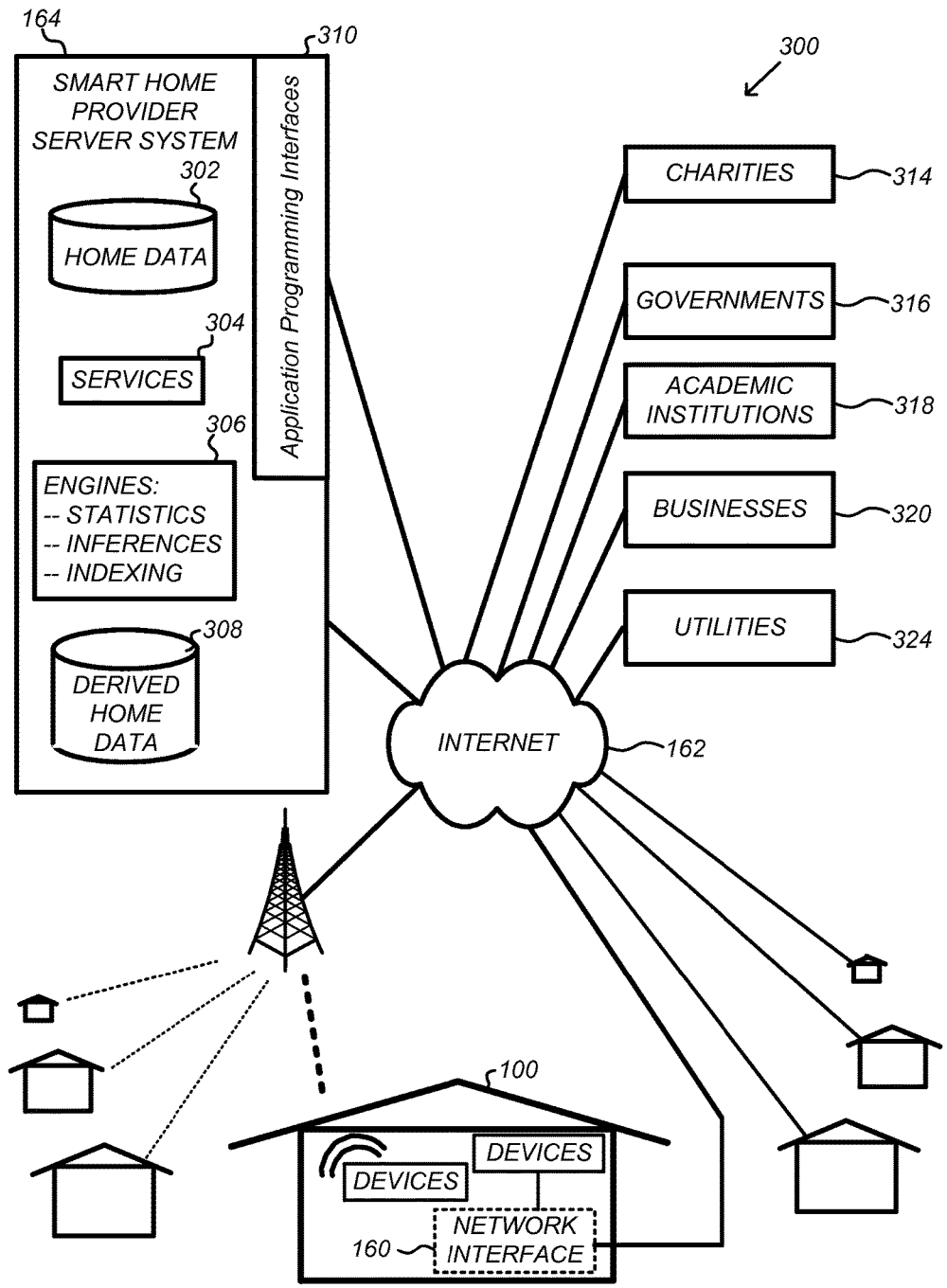
FIG. 3 illustrates a network-level view of an extensible devices and services platform with which the smart home environment of FIG. 1 is integrated, in accordance with some embodiments.

FIG. 3 illustrates a network-level view of an extensible devices and services platform with which the smart home environment of FIG. 1 is integrated, in accordance with some embodiments. The extensible devices and services platform 300 includes smart home provider server system 164. Each of the intelligent, network-connected devices described with reference to FIG. 1 (e.g., 102, 104, 106, 108, 110, 112, 114, 116 and 118, identified simply as "devices" in FIGS. 2-4) may communicate with the smart home provider server system 164. For example, a connection to the Internet 162 may be established either directly (for example, using 3G/4G connectivity to a wireless carrier), or through a network interface 160 (e.g., a router, switch, gateway, hub, or an intelligent, dedicated whole-home controller node), or through any combination thereof.

In some embodiments, the devices and services platform 300 communicates with and collects data from the smart devices of the smart home environment 100. In addition, in some embodiments, the devices and services platform 300 communicates with and collects data from a plurality of smart home environments 100 across the world. For example, the smart home provider server system 164 collects home data 302 from the devices of one or more smart home environments 100, where the devices may routinely transmit home data or may transmit home data in specific instances (e.g., when a device queries the home data 302). Exemplary collected home data 302 includes, without limitation, power consumption data, occupancy data, HVAC settings and usage data, levels of detected gasses (e.g., carbon monoxide levels data, carbon dioxide levels data, volatile organic compounds levels data, etc.), levels of detected particulates, sleeping schedule data, cooking schedule data, inside and outside temperature humidity data, television viewership data, inside and outside noise level data, pressure data, video data, etc.

In some embodiments, the smart home provider server system 164 provides one or more services 304 to smart homes and/or third parties. Exemplary services 304 include, without limitation, software updates, customer support, sensor data collection/logging, remote access, remote or distributed control, notifications of cumulative exposure to hazardous substances, and/or use suggestions (e.g., based on collected home data 302) to improve performance, reduce utility cost, increase safety, etc. In some embodiments, data associated with the services 304 is stored at the smart home provider server system 164, and the smart home provider server system 164 retrieves and transmits the data at appropriate times (e.g., at regular intervals, upon receiving a request from a user, etc.).

In some embodiments, the extensible devices and services platform 300 includes a processing engine 306, which may be concentrated at a single server or distributed among several different computing entities without limitation. In some embodiments, the processing engine 306 includes engines configured to receive data from the devices of smart home environments 100 (e.g., via the Internet 162 and/or a network interface 160), to index the data, to analyze the data and/or to generate statistics based on the analysis or as part of the analysis. In some embodiments, the analyzed data is stored as derived home data 308.

Results of the analysis or statistics may thereafter be transmitted back to the device that provided home data used to derive the results, to other devices, to a server providing a webpage to a user of the device, or to other non-smart device entities. In some embodiments, use statistics, use statistics relative to use of other devices, use patterns, and/or statistics summarizing sensor readings are generated by the processing engine 306 and transmitted. The results or statistics may be provided via the Internet 162. In this manner, the processing engine 306 may be configured and programmed to derive a variety of useful information from the home data 302. A single server may include one or more processing engines.

The derived home data 308 may be used at different granularities for a variety of useful purposes, ranging from explicit programmed control of the devices on a per-home, per-neighborhood, or per-region basis (for example, demand-response programs for electrical utilities), to the generation of inferential abstractions that may assist on a per-home basis (for example, an inference may be drawn that the homeowner has left for vacation and so security detection equipment may be put on heightened sensitivity), to the generation of statistics and associated inferential abstractions that may be used for government or charitable purposes. For example, processing engine 306 may generate statistics about device usage across a population of devices and send the statistics to device users, service providers or other entities (e.g., entities that have requested the statistics and/or entities that have provided monetary compensation for the statistics).

In some embodiments, to encourage innovation and research and to increase products and services available to users, the devices and services platform 300 exposes a range of application programming interfaces (APIs) 310 to third parties, such as charities 314, governmental entities 316 (e.g., the Food and Drug Administration or the Environmental Protection Agency), academic institutions 318 (e.g., university researchers), businesses 320 (e.g., providing device warranties or service to related equipment, targeting advertisements based on home data), utility companies 324, and other third parties. The APIs 310 are coupled to and permit third-party systems to communicate with the smart home provider server system 164, including the services 304, the processing engine 306, the home data 302, and the derived home data 308. In some embodiments, the APIs 310 allow applications executed by the third parties to initiate specific data processing tasks that are executed by the smart home provider server system 164, as well as to receive dynamic updates to the home data 302 and the derived home data 308.

For example, third parties may develop programs and/or applications, such as web applications or mobile applications, that integrate with the smart home provider server system 164 to provide services and information to users. Such programs and applications may be, for example, designed to help users reduce energy consumption, to preemptively service faulty equipment, to prepare for high service demands, to track past service performance, to track cumulative exposure to hazardous substances, and/or to perform other beneficial functions or tasks.

Figure 4:
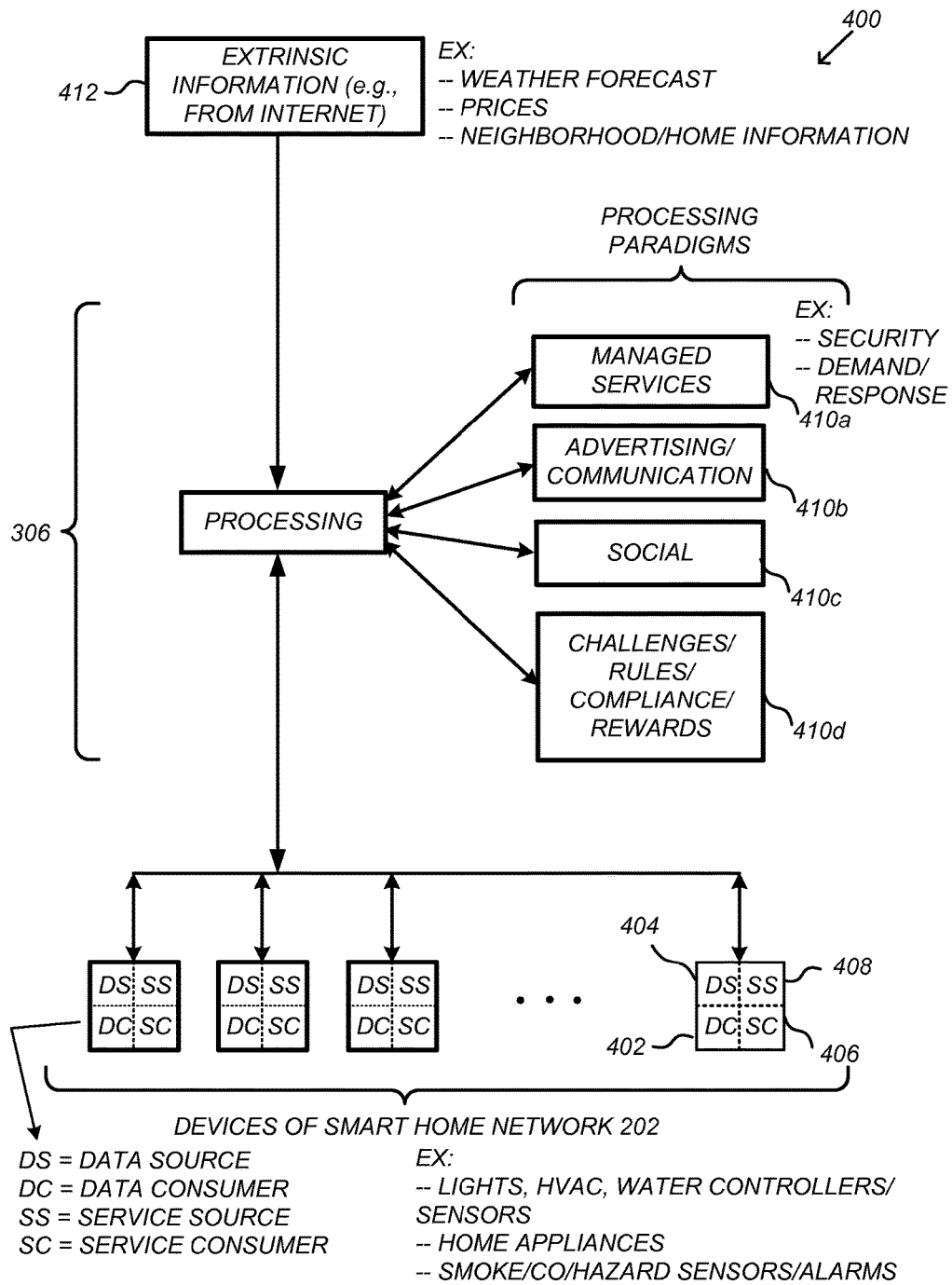
FIG. 4 illustrates an abstracted functional view of the extensible devices and services platform of FIG. 3, with reference to a processing engine as well as devices of the smart home environment, in accordance with some embodiments.

FIG. 4 illustrates an abstracted functional view 400 of the extensible devices and services platform 300 of FIG. 3, with reference to a processing engine 306 as well as devices of the smart home environment, in accordance with some embodiments. Even though devices situated in smart home environments will have a wide variety of different individual capabilities and limitations, the devices may be thought of as sharing common characteristics in that each device is a data consumer 402 (DC), a data source 404 (DS), a services consumer 406 (SC), and/or a services source 408 (SS). Advantageously, in addition to providing control information used by the devices to achieve their local and immediate objectives, the extensible devices and services platform 300 may also be configured to use the large amount of data that is generated by these devices. In addition to enhancing or optimizing the actual operation of the devices themselves with respect to their immediate functions, the extensible devices and services platform 300 may be directed to "repurpose" that data in a variety of automated, extensible, flexible, and/or scalable ways to achieve a variety of useful objectives. These objectives may be predefined or adaptively identified based on, e.g., usage patterns, device efficiency, and/or user input (e.g., requesting specific functionality).

FIG. 4 shows processing engine 306 as including a number of processing paradigms 410. In some embodiments, processing engine 306 includes a managed services paradigm 410a that monitors and manages primary or secondary device functions. The device functions may include ensuring proper operation of a device given user inputs, estimating that (e.g., and responding to an instance in which) a cumulative exposure of an occupant to a harmful substance satisfies a threshold, and/or providing an alert regarding the cumulative exposure of the occupant. In some embodiments, processing engine 306 includes an advertising/communication paradigm 410b that estimates characteristics (e.g., demographic information), desires and/or products of interest of a user based on device usage. Services, promotions, products or upgrades may then be offered or automatically provided to the user. In some embodiments, processing engine 306 includes a social paradigm 410c that uses information from a social network, provides information to a social network (for example, based on device usage), and/or processes data associated with user and/or device interactions with the social network platform. For example, a user's status as reported to their trusted contacts on the social network may be updated to indicate when the user is home based on light detection, security system inactivation, device usage detectors, or occupancy sensors. As another example, the cumulative exposure of a user (i.e., an occupant) to a hazardous substance may be shared with one or more other users (e.g., with users specified as trusted contacts due to their status as caregivers).

In some embodiments, processing engine 306 includes a challenges/rules/compliance/rewards paradigm 410d that informs a user of challenges, competitions, rules, compliance regulations and/or rewards and/or that uses operation data to determine whether a challenge has been met, a rule or regulation has been complied with and/or a reward has been earned. The challenges, rules, and/or regulations may relate to efforts to conserve energy, to live safely (e.g., reducing exposure to hazardous substances such as toxins, carcinogens, etc.), to conserve money and/or equipment life, to improve health, etc. For example, one challenge may involve participants remediating a level of a hazardous substance (e.g., concentration of a toxic/noxious gas or harmful particulate) in a home or other structure. Those participants that successfully complete the challenge are rewarded, such as with coupons, virtual currency, status, etc. Regarding compliance, an example involves ensuring that cumulative exposure of an occupant to a hazardous substance stays within a range that is considered safe.

In some embodiments, processing engine 306 integrates or otherwise uses extrinsic information 412 from extrinsic sources to improve the functioning of one or more processing paradigms. Extrinsic information 412 may be used to interpret data received from a device, to determine a characteristic of the environment near the device (e.g., outside a structure that the device is enclosed in), to determine services or products available to the user, to identify a social network or social-network information, to determine contact information of entities (e.g., emergency services such as an emergency-response team, the police or a hospital) near the device, to identify statistical or environmental conditions, trends or other information associated with a home or neighborhood, and so forth.

FIG. 5 is a block diagram illustrating an exemplary smart device 204 (e.g., a smart hazard detector 104) (e.g., a camera 118 or other occupancy sensor) in accordance with some embodiments. The smart device 204 typically includes one or more processing units (processors or cores) 502, one or more network or other communications interfaces 504, memory 506, and one or more communication buses 508 for interconnecting these components. The communication buses 508 optionally include circuitry (sometimes called a chipset) that interconnects and controls communications between system components. In some embodiments, the smart device 204 includes a user interface 510. The user interface 510 may include a display device 512. In some embodiments, the smart device 204 includes one or more inputs 516 (e.g., input buttons, a keyboard, a mouse, and/or other inputs). In some embodiments, the smart device 204 includes a 3D gesture sensor for touchless gesture control. Alternatively or in addition, in some embodiments, the display device 512 includes a touch-sensitive surface 514, in which case the display device 512 is a touch-sensitive display. In some embodiments, the user interface 510 also includes an audio output device 518, such as speakers or an audio output connection connected to speakers, earphones, or headphones. Furthermore, some smart devices 204 use a microphone and voice recognition to supplement or replace the keyboard. Optionally, the smart device 204 includes an audio input device 520 (e.g., a microphone) to capture audio (e.g., speech from a user). Optionally, the smart device 204 includes a location detection device 522, such as a GPS (global positioning satellite) or other geo-location receiver, for determining the location of the smart device 204. The smart device 204 also optionally includes an image/video capture device 524 (e.g., a camera 118), which may serve as an occupancy sensor.

In some embodiments, the smart device 204 includes one or more hazardous substance sensors 523 (e.g., gas sensors and/or particulate detectors). In some embodiments, the smart device 204 includes one or more occupancy sensors 525 (e.g., a passive IR motion sensor in addition to or as an alternative to the image/video capture device 524).

Memory 506 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 506 may optionally include one or more storage devices remotely located from the processor(s) 502. Memory 506, or alternately the non-volatile memory device(s) within memory 506, includes a non-transitory computer readable storage medium. In some embodiments, memory 506 or the computer readable storage medium of memory 506 stores the following programs, modules and data structures, or a subset or superset thereof:

- an operating system 526 that includes procedures for handling various basic system services and for performing hardware-dependent tasks;
- a network communication module 528 that is used for connecting the smart device 204 to other computers via the one or more communication network interfaces 504 (wired or wireless) and one or more communication networks, such as smart home network 202 (e.g., a mesh network), the Internet 162, cellular telephone networks, mobile data networks, other wide area networks, local area networks, metropolitan area networks, and so on;
- an image/video capture module 530 (e.g., a camera module) for processing a respective image or video captured by the image/video capture device 524, where the respective image or video may be sent or streamed through the smart home network 202 to a portable electronic device 166, smart home provider server system 164, other smart device 204, and/or other computing system;
- an audio input module 532 (e.g., a microphone module) for processing audio captured by the audio input device 520, where the respective audio may be sent or streamed through the smart home network 202 to a portable electronic device 166, smart home provider server system 164, other smart device 204, and/or other computing system;
- a hazardous-substance detection module 534 for processing data captured by the hazardous-substance sensor 523, where the data may be sent or streamed through the smart home network 202 to a portable electronic device 166, smart home provider server system 164, other smart device 204, and/or other computing system;
- an occupancy data module 536 for processing data captured by the image/video capture device 524 and/or occupancy sensor 525, where the data may be sent or streamed through the smart home network 202 to a portable electronic device 166, smart home provider server system 164, other smart device 204, and/or other computing system;
- a location detection module 538 (e.g., a GPS, Wi-Fi, or hybrid positioning module) for determining the location of the smart device 204 (e.g., using the location detection device 522) and providing this location information through the smart home network 202 to a portable electronic device 166, smart home provider server system 164, other smart device 204, and/or other computing system; and
- one or more application modules 540, including the following modules (or sets of instructions), or a subset or superset thereof:
  - a smart home module 542 for providing an interface to a smart home application (e.g., a stand-alone application or an application in communication with another device in smart home network 202 and/or smart home provider server system 164) and related features;
  - an occupancy-determination module 544 for determining occupancy of a room in the structure 150 in which the smart device 204 is located, and/or respective rooms 152 of the structure 150 (e.g., based on occupancy data received from smart devices 204 in different rooms 152); and/or
  - a cumulative exposure determination module 546 to determine cumulative exposure to one or more hazardous substances (e.g., using occupancy information as determined using the occupancy-determination module 544 and data from hazardous-substance detection modules 534 of respective smart devices 204).

In some embodiments, the cumulative exposure determination module 546 includes instructions to determine cumulative exposure that occurs within the room 152 in which the smart device 204 of FIG. 5 is located, but not cumulative exposure that occurs within other rooms 152 in the structure 150. The smart device 204 of FIG. 5 provides this data to a separate computing system (e.g., a computing system 600, FIG. 6), which receives similar data on cumulative exposure in respective rooms 152 from other smart devices 204 and determines a total cumulative exposure that occurs within the structure 150. Alternatively, the cumulative exposure determination module 546 includes instructions for determining the total cumulative exposure that occurs within the structure 150, based on exposure and occupancy data collected by multiple smart devices 204.

FIG. 6 is a block diagram illustrating an exemplary computing system 600 in accordance with some embodiments. In some embodiments, the computing system 600 is a computer or other portable electronic device 166. In some embodiments, the computing system 600 is the smart home provider server system 164 or another server system outside of the structure 150. In some embodiments, the computing system 600 is a stand-alone controller (e.g., located in the structure 150) that is distinct from the smart devices 204 and the smart home provider server system 164. In some embodiments, the computing system 600 is a smart device 204 (e.g., with additional components as shown in FIG. 5) or a collection of multiple smart devices 204. For example, the computing system 600 may have a housing that contains the components shown in FIG. 6 and also contains a smart hazard detector 204 and/or at least one occupancy sensor (e.g., a camera 118 or other occupancy sensor).

The computing system 600 typically includes one or more processing units (processors or cores) 602, one or more network or other communications interfaces 604, memory 606, and one or more communication buses 608 for interconnecting these components. The communication buses 608 optionally include circuitry (sometimes called a chipset) that interconnects and controls communications between system components. In some embodiments, the computing system 600 includes a user interface 605 (e.g., which is analogous to the user interface 510, FIG. 5).

Memory 606 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 606 may optionally include one or more storage devices remotely located from the processor(s) 602. Memory 606, or alternately the non-volatile memory device(s) within memory 606, includes a non-transitory computer readable storage medium. In some embodiments, memory 606 or the computer readable storage medium of memory 606 stores the following programs, modules and data structures, or a subset or superset thereof:

- an operating system 610 that includes procedures for handling various basic system services and for performing hardware-dependent tasks;

a network communication module 612 that is used for connecting the computing system 600 to other computers via the one or more communication network interfaces 604 (wired or wireless) and one or more communication networks, such as smart home network 202 (e.g., a mesh network), the Internet 162, cellular telephone networks, mobile data networks, other wide area networks, local area networks, metropolitan area networks, and so on;

a database 614 that includes the following data:
   occupancy information 616 (e.g., received from occupancy data modules 536 in respective smart devices 204, FIG. 5); and/or
   hazardous substance detection information 618 (e.g., received from hazardous substance detection modules 534 in respective smart devices 204, FIG. 5);

one or more application modules 620, including the following modules (or sets of instructions), or a subset or superset thereof:
   an occupancy-determination module 622 for determining occupancy of the structure 150 and/or respective rooms 152 of the structure 150 (e.g., based on the occupancy information 616 in the database 614); and/or
   a cumulative exposure determination module 624 to determine cumulative exposure to one or more hazardous substances (e.g., based on the hazardous substance detection information 618 in the database 614 along with the occupancy determined by the occupancy-determination module 622).

Each of the above identified modules and applications of FIGS. 5 and 6 correspond to a set of executable instructions for performing one or more functions described above and the methods described in this application (e.g., the computer-implemented methods and other information processing methods described herein). These modules (i.e., sets of instructions) need not be implemented as separate software programs, procedures or modules, and thus various subsets of these modules are, optionally, combined or otherwise re-arranged in various embodiments. In some embodiments, memory 506 and/or 606 store a subset of the modules and data structures identified above. Furthermore, memory 506 and/or 606 optionally store additional modules and data structures not described above. In some embodiments, these modules and data structures, or a subset thereof, are implemented in hardware or in a combination of hardware and software.

Attention is now directed towards embodiments of graphical user interfaces ("GUIs") and associated processes that may be implemented on an electronic device to provide information regarding cumulative exposure to one or more hazardous substances.

FIGS. 7A-7C illustrate exemplary GUIs 704 (FIG. 7A), 720 (FIG. 7B), and 730 (FIG. 7C) displayed on a portable electronic device 166 (or other computing system) in accordance with some embodiments. The GUIs of FIGS. 7A-7C are used to illustrate operations in the methods 800 (FIG. 8) and 900 (FIGS. 9A-9B). The GUIs 704, 720, and 730 are displayed on a screen 702. In some embodiments, the screen 702 is an example of a user interface 605 (FIG. 6). In some embodiments, the screen 702 is an example of a display 512 (FIG. 5) of a smart device 204. In some embodiments, the GUIs 704, 720, and 730 are generated based on information from a computing system 600.

The GUI 704 (FIG. 7A) shows an exposure report for carbon monoxide (CO). Similar exposure reports may be displayed for other toxic/noxious gasses. The exposure report includes a warning 706 that cumulative exposure to CO has satisfied a specified threshold (e.g., has exceeded a safe level). The exposure report also includes a command 708 telling the user to leave the house and/or statement 710 of the determined cumulative exposure to CO and the cumulative-exposure threshold for CO (e.g., the level considered safe). In the example of FIG. 7A, the determined cumulative exposure and the cumulative-exposure threshold are time-weighted average (TWA) values.

The GUI 720 (FIG. 7B) shows another CO exposure report, which includes a statement 722 that cumulative exposure to CO has not satisfied a specified threshold (e.g., is within safe levels). The GUI 720 also includes statements 724 of the determined cumulative exposure to CO and the cumulative-exposure threshold for CO. Because the specified threshold has not been satisfied, the GUI 720 does not include a command 708.

The GUI 740 (FIG. 7C) shows an exposure report for pollen. Similar exposure reports may be displayed for other harmful particulates. The exposure report includes a warning 732 that cumulative exposure to pollen has satisfied a specified threshold (e.g., has exceeded a safe level). The exposure report also includes a command 734 telling the user to shelter in a room with filtered air. In this example, the command 734 does not tell the user to leave the house, because a high pollen level in the house would likely correspond to a high pollen level outside the house. The exposure report may further include notifications (not shown) of the determined cumulative exposure to pollen and the cumulative-exposure threshold for pollen.

The commands 708 and 734 are merely examples of possible commands. Other examples include, without limitation, telling the occupant to leave a particular room or part of the house (e.g., to leave the basement in the case of radon exposure), to contact emergency services, or to seek medical attention. Furthermore, commands may be directed to a caregiver (e.g., a parent or nurse) or other person responsible for the occupant, instead of or in addition to the occupant. For example, a command may tell the caregiver to check on the occupant, to remove the occupant from the house or a portion thereof, or to move the occupant to a specific room in the house.

FIG. 8 is a flow diagram illustrating a method 800 of determining and acting upon cumulative exposure of a building occupant to a hazardous substance, in accordance with some embodiments. Respective portions of the method 800 are performed by smart devices 204 (FIGS. 2, 5) and a computing system 600 (FIG. 6). The method 800 corresponds to instructions stored in one or more non-transitory computer-readable storage media. For example, the portions performed by smart devices 204 correspond to instructions stored in memories 506 (FIG. 5) and the portions performed by the computing system 600 correspond to instructions stored in the memory 606 (FIG. 6). Examples and details of the portion of the method 800 performed by the computing system 600 are provided below in the method 900 (FIGS. 9A-9B).

Stationary gas sensors (e.g., smart hazard detectors 104 located in fixed locations) send (802) data that correspond to local concentrations (e.g., in real time) of a gas in a home. The local concentrations may be concentrations in respective rooms 152 or portions of rooms, as measured by the gas sensors. The computing system 600 receives this data from a plurality of the stationary gas sensors in the home.

Occupancy sensors (e.g., cameras 118 or other occupancy sensors) send (806) data that correspond to occupancy of the home, including occupancy by a first occupant. The data indicates, for example, periods of time in which the first occupant is in the structure 150 or in respective rooms 152 of the structure 150. The computing system 600 receives (808) this data from the occupancy sensors.

The computing system 600 determines (810), based at least in part on the received data that correspond to local concentrations of the gas and the received data that correspond to occupancy of the home, a cumulative exposure of the first occupant to the gas in the home. Examples of the operation 810 are provided below with respect to operation 914 (FIG. 9A) of the method 900.

The computing system 600 performs and/or sends instructions to perform (812) one or more predefined operations in accordance with the determined cumulative exposure of the first occupant. In some embodiments, the computing system 600 may perform and/or send instructions to perform (814) the one or more predefined operations periodically, on an event-triggered basis (e.g., in response to the cumulative exposure satisfying a threshold), or both periodically and on an event-triggered basis. Examples of the operation 812 are provided below with respect to operation 918 (FIG. 9B) of the method 900.

FIGS. 9A and 9B are flow diagrams illustrating a method 900 of determining and acting upon cumulative exposure of a building occupant to a hazardous substance, in accordance with some embodiments. The method 900 is performed by a computing system 600 (FIG. 6) and corresponds to instructions stored in a non-transitory computer-readable storage medium (e.g., memory 606, FIG. 6). Operations 902, 904, 914, and 918 of the method 900 correspond respectively to operations 804, 808, 810, and 812 of the method 800 (FIG. 8).

The computing system 600 receives (902, FIG. 9A) data that correspond to local concentrations of a gas from a plurality of stationary gas sensors (e.g., smart hazard detectors 104 located in fixed locations) in a home (or other structure 150). The stationary gas sensors are located in a plurality of rooms 152 in the home. A respective stationary gas sensor is located at a respective fixed location in a respective room 152 in the home. This data may include instantaneous concentrations measured over time (e.g., periodically).

The computing system 600 receives (904) data that correspond to occupancy of the home, including occupancy by a first occupant. This data is received from occupancy sensors (e.g., cameras 118, smart doorbell 106, smart doorlocks, touch screens, IR sensors, microphones, ambient light sensors, motion detectors, smart nightlights 170, etc.).

In some embodiments, the data that correspond to occupancy of the home includes (906) an arrival time for the first occupant in the home. In some embodiments, the data includes multiple arrival times and/or departure times for the first occupant, if the first occupant leaves and returns.

In some embodiments, the data that correspond to occupancy of the home includes (908) respective time spent by the first occupant in respective rooms of the home since the first occupant arrived in the home.

In some embodiments, the data that correspond to occupancy of the home includes (910) respective time spent by a mobile phone (or other portable electronic device) of the first occupant in respective rooms of the home since the first occupant arrived in the home. The mobile phone (or other portable electronic device) may serve as a proxy for the first occupant if carried by the first occupant.

In some embodiments, the data that correspond to occupancy of the home is derived (912) from one or more of: (i) processing information derived from video cameras (e.g., cameras 118, FIG. 1) distributed in respective rooms of the home to identify the occupant therein; (ii) processing information derived from signals emitted from a mobile phone or wearable electronic device (e.g., portable electronic device 166) on the occupant for identifying the identity and location of the occupant within the home; and (iii) processing information derived from passive electromagnetic signature tags (e.g., RFID tags) located on or within the occupant for identifying the identity and location of the occupant within the home. This information may be processed by respective smart devices 204 and then sent to the computing system 600, or may be processed by the computing system 600.

The computing system 600 determines (914), based at least in part on the received data that correspond to local concentrations of the gas and the received data that correspond to occupancy of the home, a cumulative exposure of the first occupant to the gas in the home.

In some embodiments, the computing system 600 uses (916) a time-weighted-average (TWA) exposure model to determine the cumulative exposure of the first occupant. For example, the computing system 600 integrates instantaneous concentrations in each room over the time period that the first occupant spends in each room to determine a TWA exposure for each room, and then takes an average of the TWA exposures of each room weighted by the time that the occupant spent in each room.

In some embodiments, the reading(s) for establishing a particular concentration metric at a particular time (e.g., a particular instantaneous concentration) are based on the reading of the detector that is in closest physical proximity to the occupant, rather than the detector corresponding to the particular room being occupied. While the same detector will often be both closest to the user and in the room being occupied, this is not always the case, for example when the occupant is standing near a doorway between two rooms. In some embodiments, an instantaneous evaluation can be made regarding which detector's readings to use when the occupant is standing near (e.g., within a specified distance of) a doorway. For example, in a single-doored room, if the door of the currently-occupied room is closed (as sensed by a camera or door sensor or other smart-home sensor device), then the concentration reading of the detector in the currently-occupied room is used, no matter how close the occupant is to the doorway. If the door is open, however, then the reading from the closest detector to the occupant (which might be in the adjacent room) is used. In some embodiments, a distance-weighted average of the concentrations taken from the two closest detectors to the occupant is calculated. In the more general case, a distance-weighted average of the concentrations taken from the N closest detectors to the occupant is calculated, where N is an integer greater than or equal to two. A variety of different methods for tracking the particular position of the occupant within a room can be used including, but not limited to, video cameras, IR sensors, ultrasound sensors, heat sensors, CO2 sensors (higher CO2 concentrations near the occupant due to breathing), RFID sensors, and other sensors. For the case in which the occupant is a pet (and potentially for humans), a subcutaneous RFID chip can be used for determining specific occupant position.

In some embodiments, the computing system 600 uses (916) a dosimetry model to determine the cumulative exposure of the first occupant. For example, the data from the plurality of stationary gas sensors and the occupancy data are used to estimate a dose deposited on the breathing airway surfaces in the respiratory tract of the first occupant. Absorption and transport of the dose are then estimated using an anatomical model of the respiratory tract (e.g., a lower respiratory tract (LRT) model). The dosimetry model may also account for chemical reactions involving the dose in the first occupant and/or purging of at least some of the dose from the first occupant.

In some embodiments, the cumulative exposure of the first occupant is determined starting from the first occupant's arrival at the home. The cumulative exposure thus may be set to zero upon the first occupant's arrival. If the first occupant subsequently leaves and then returns, however, the cumulative exposure is not reset to zero in accordance with some embodiments. In some embodiments, the cumulative exposure upon the first occupant's return is set equal to the cumulative exposure when the first occupant left. In some embodiments, the cumulative exposure upon the first occupant's return is set equal to the cumulative exposure when the first occupant left minus an amount estimated to have been purged from the first occupant during the time that the first occupant was away from the home (e.g., using a dosimetry model). Alternatively, in some embodiments, the cumulative exposure is reset to zero each time the first occupant arrives at the home.

In some embodiments in which the location of a phone (or other portable electronic device 166) is used to determine occupancy information, and is thereby used in determining cumulative exposure, a determination is first made as to whether the location of the phone is a reasonable proxy for the location of the first occupant. For example, if the phone remains stationary for more than a specified, extended period of time (e.g., a period of time that does not correspond to a known sleep schedule of the first occupant), then it is assumed that the phone's location is not a reasonable proxy for the first occupant's location, and the phone location data is not used as occupancy data.

The computing system 600 performs and/or sends instructions to perform (918, FIG. 9B) one or more predefined operations in accordance with the determined cumulative exposure of the first occupant. For example, the computing system 600 determines (920) whether the cumulative exposure of the first occupant satisfies predefined cumulative-exposure criteria. If the predefined cumulative-exposure criteria are satisfied (920-Yes), the computing system 600 may send (922) instructions to activate (e.g., sound) an alarm to devices containing the plurality of stationary gas sensors (e.g., to smart hazard detectors 104) and/or other smart devices 204, may send (924) a notification to a phone or other electronic device (e.g., device 166) associated with the first occupant, and/or may send (926) a notification to a phone or other electronic device associated with a caregiver of the first occupant. In some embodiments, the notification sent (924, 926) to the phone or other electronic device (e.g., device 166) associated with the first occupant and/or caregiver includes a warning (e.g., 706, FIG. 7A), command (e.g., 708, FIG. 7A), and/or statement (e.g., 710, FIG. 7A). Examples of the notification include a text message, an automated voice message, and an email. Furthermore, multiple notifications of different types (e.g., text messages, automated voice messages, and/or email) may be sent. (If the computing system 600 is a respective smart device 204, it may sound an alarm itself. If the computing system 600 is the phone or other electronic device of the first occupant or the caregiver, the computing system 600 may display the notification itself.)

In some embodiments, if the predefined cumulative-exposure criteria are satisfied, the computing system 600 may send a message to emergency services (e.g., summoning emergency services to the home) and/or to a government agency.

If the predefined cumulative-exposure criteria are not satisfied, the computing system 600 continues to determine and monitor the cumulative exposure of the first occupant. The computing system 600 also may send a notification (e.g., including statements 722 and/or 724, FIG. 7B) to the phone or other electronic device of the first occupant and/or the caregiver.

In some embodiments, the computing system 600 performs and/or sends the instructions to perform (928) the one or more predefined operations in accordance with predefined criteria that are tailored to the first occupant. For example, a threshold applied as the cumulative-exposure criteria of operation 920 may be tailored to the first occupant. The value of the threshold may be based, for example, on the age, weight, health (e.g., including physical condition and/or known sensitivities), and/or other physical characteristics of the first occupant. The threshold for cumulative exposure of an infant or elderly person may be lower than the threshold for a (non-elderly) adult. Increased weight may correspond to an increased threshold. A known health condition or sensitivity to a hazardous substance may result in a lower threshold. In some embodiments, the threshold for the first occupant is entered via a settings interface in the computing system 600. Alternatively, data regarding the personal characteristics is entered through the settings interface and is used by the computing system 600 to determine the threshold.

While the methods 800 and 900 refer to gas, similar methods may be performed involving other hazardous substances (e.g., particulates).

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to limit the scope of the claims to the precise forms disclosed. Many modifications and variations are possible in view of the above teachings. The embodiments were chosen in order to best explain the principles underlying the claims and their practical applications, to thereby enable others skilled in the art to best use the embodiments with various modifications as are suited to the particular uses contemplated.

What is claimed is:
1. A method, comprising:
  at a computing device associated with a smart home environment:
    receiving, from a plurality of stationary gas sensors communicatively coupled to the computing device, data that correspond to local concentrations of a gas in respective rooms of a home associated with the smart home environment; wherein:
      the stationary gas sensors are located in a plurality of the respective rooms in the home, and a respective stationary gas sensor is located at a respective fixed location in a respective room in the home;

receiving data that correspond to occupancy of a first occupant of the home, including location data indicating respective periods of time in which the first occupant is present in each respective room of the home;

determining, based at least in part on (i) the received data that correspond to local concentrations of the gas in respective rooms of the home and (ii) the received data that correspond to occupancy of the first occupant in respective rooms of the home, a cumulative exposure of the first occupant to the gas in the home;

selecting one of a plurality of predefined operations in accordance with the determined cumulative exposure of the first occupant and one or more of: (i) a characteristic of the gas associated with the cumulative exposure, or (ii) predefined criteria that are tailored to the first occupant; and performing and/or sending instructions to perform the selected predefined operation.

2. The method of claim 1, wherein the data that correspond to occupancy of the first occupant of the home includes an arrival time for the first occupant in the home.

3. The method of claim 1, wherein the data that correspond to occupancy of the first occupant of the home includes respective time spent by the first occupant in respective rooms of the home since the first occupant arrived in the home.

4. The method of claim 1, wherein the data that correspond to occupancy of the first occupant of the home includes respective time spent by a mobile phone of the first occupant in respective rooms of the home since the first occupant arrived in the home.

5. The method of claim 1, wherein the data that correspond to occupancy of the first occupant of the home is derived from one or more of:

processing information derived from video cameras distributed in respective rooms of the home to identify the first occupant therein;

processing information derived from signals emitted from a mobile phone or wearable electronic device on the first occupant for identifying the identity and location of the first occupant within the home; and/or processing information derived from passive electromagnetic signature tags located on or within the first occupant for identifying the identity and location of the first occupant within the home.

6. The method of claim 1, wherein determining the cumulative exposure of the first occupant to the gas in the home comprises:

integrating instantaneous concentrations of gas in each room over time periods during which the first occupant occupies each room to determine respective exposure values for each respective room; and averaging the respective exposure values weighted by respective times spent by the first occupant in each respective room.

7. The method of claim 1, further comprising:

obtaining one or more physical characteristics of the first occupant; and determining a cumulative exposure threshold value based on the one or more physical characteristics of the first occupant;

wherein the selecting of one of the plurality of predefined operations is in accordance with (ii) predefined criteria that are tailored to the first occupant, wherein the predefined criteria are based on the determined cumulative exposure threshold value.

8. The method of claim 1, wherein performing and/or sending instructions to perform one or more predefined operations in accordance with the determined cumulative exposure of the first occupant comprises:

determining whether the cumulative exposure of the first occupant meets first predefined cumulative exposure criteria; and in accordance with determining that the cumulative exposure of the first occupant meets the first predefined cumulative exposure criteria, sending instructions to sound an alarm to devices containing the plurality of stationary gas sensors.

9. The method of claim 1, wherein performing and/or sending instructions to perform one or more predefined operations in accordance with the determined cumulative exposure of the first occupant includes:

determining whether the cumulative exposure of the first occupant meets first predefined cumulative exposure criteria; and in accordance with determining that the cumulative exposure of the first occupant meets the first predefined cumulative exposure criteria, sending a notification to a phone associated with the first occupant.

10. The method of claim 1, wherein performing and/or sending instructions to perform one or more predefined operations in accordance with the determined cumulative exposure of the first occupant includes:

determining whether the cumulative exposure of the first occupant meets first predefined cumulative exposure criteria; and in accordance with determining that the cumulative exposure of the first occupant meets the first predefined cumulative exposure criteria, sending a notification to a phone associated with a caregiver of the first occupant.

11. The method of claim 1, wherein a housing that contains the computing device also contains one of the plurality of stationary gas sensors.

12. The method of claim 1, wherein a housing that contains the computing device also contains one of the plurality of stationary gas sensors and at least one sensor that provides data that correspond to occupancy of the home.

13. The method of claim 1, wherein the computing device is located in the home at a separate location from locations of the plurality of stationary gas sensors in the home.

14. The method of claim 1, wherein the computing device is located in a server system remote from the home.

15. A computing system, comprising:

one or more processors; and memory storing one or more programs configured to be executed by the one or more processors, the one or more programs including instructions for:

receiving, from a plurality of stationary gas sensors communicatively coupled to a computing device associated with a smart home environment, data that correspond to local concentrations of a gas in respective rooms of a home associated with the smart home environment; wherein:

the stationary gas sensors are located in a plurality of the respective rooms in the home, and a respective stationary gas sensor is located at a respective fixed location in a respective room in the home;

receiving data that correspond to occupancy of a first occupant of the home, including location data indicating periods of time in which the first occupant is in respective rooms of the home;

determining, based at least in part on (i) the received data that correspond to local concentrations of the gas in respective rooms of the home and (ii) the received data that correspond to occupancy of the first occupant in respective rooms of the home, a cumulative exposure of the first occupant to the gas in the home;

selecting one of a plurality of predefined operations in accordance with the determined cumulative exposure of the first occupant and one or more of: (i) a characteristic of the gas associated with the cumulative exposure, or (ii) predefined criteria that are tailored to the first occupant; and performing and/or sending instructions to perform the selected predefined operation.

16. A non-transitory computer-readable storage medium storing one or more programs, the one or more programs comprising instructions, which when executed by a computing system, cause the computing system to:

receive, from a plurality of stationary gas sensors communicatively coupled to a computing device associated with a smart home environment, data that correspond to local concentrations of a gas in respective rooms of a home associated with the smart home environment; wherein:

the stationary gas sensors are located in a plurality of the respective rooms in the home, and a respective stationary gas sensor is located at a respective fixed location in a respective room in the home;

receive data that correspond to occupancy of a first occupant of the home, including location data indicating periods of time in which the first occupant is in respective rooms of the home;

determine, based at least in part on (i) the received data that correspond to local concentrations of the gas in respective rooms of the home and (ii) the received data that correspond to occupancy of the first occupant in respective rooms of the home, a cumulative exposure of the first occupant to the gas in the home;

select one of a plurality of predefined operations in accordance with the determined cumulative exposure of the first occupant and one or more of: (i) a characteristic of the gas associated with the cumulative exposure, or (ii) predefined criteria that are tailored to the first occupant; and perform and/or send instructions to perform the selected predefined operation.

* * * * *